United States Patent
Grosjacques et al.

(10) Patent No.: US 10,639,262 B2
(45) Date of Patent: May 5, 2020

(54) TONING SHAMPOO WITH IMPROVED COLOUR PERFORMANCE

(71) Applicant: Henkel AG & Co. KGaA, Duesseldorf (DE)

(72) Inventors: Camille Grosjacques, Hamburg (DE); Yvonne Lissner, Hamburg (DE); Susanne Bietz, Elmshorn (DE); Katharina Krause, Hamburg (DE)

(73) Assignee: Henkel AG & Co. KGaA, Dusseldorf (DE)

( * ) Notice: Subject to any disclaimer, the term of this patent is extended or adjusted under 35 U.S.C. 154(b) by 0 days.

(21) Appl. No.: 16/225,690

(22) Filed: Dec. 19, 2018

(65) Prior Publication Data

US 2019/0183768 A1 Jun. 20, 2019

(30) Foreign Application Priority Data

Dec. 20, 2017 (DE) .................. 10 2017 223 419

(51) Int. Cl.
| | |
|---|---|
| *A61Q 5/10* | (2006.01) |
| *A61K 8/60* | (2006.01) |
| *A61K 8/31* | (2006.01) |
| *A61K 8/49* | (2006.01) |
| *A61K 8/19* | (2006.01) |
| *A61Q 5/06* | (2006.01) |
| *A61K 8/44* | (2006.01) |
| *A61Q 5/02* | (2006.01) |

(52) U.S. Cl.
CPC .............. *A61K 8/604* (2013.01); *A61K 8/19* (2013.01); *A61K 8/31* (2013.01); *A61K 8/442* (2013.01); *A61K 8/494* (2013.01); *A61Q 5/02* (2013.01); *A61Q 5/065* (2013.01); *A61Q 5/10* (2013.01); *A61K 2800/43* (2013.01); *A61K 2800/432* (2013.01); *A61K 2800/592* (2013.01)

(58) Field of Classification Search
CPC .... A61Q 5/065; A61Q 5/02; A61K 2800/432; A61K 2800/43; A61K 8/46; A61K 8/604; A61K 2800/5424; A61K 8/602; A61K 8/45; A61K 2800/5428; A61K 47/14; A61K 8/4993; A61K 47/186; A61K 8/442
See application file for complete search history.

(56) References Cited

U.S. PATENT DOCUMENTS

| | | | |
|---|---|---|---|
| 7,674,299 B2 | 3/2010 | Huet et al. | |
| 8,858,652 B2 | 10/2014 | Witte et al. | |
| 2006/0100114 A1 | 5/2006 | Molenda et al. | |
| 2008/0282481 A1* | 11/2008 | De Boni | A61K 8/817 8/405 |
| 2014/0137342 A1* | 5/2014 | Guerin | A61K 8/4926 8/405 |

FOREIGN PATENT DOCUMENTS

| | | |
|---|---|---|
| DE | 19741162 A1 | 4/1999 |
| DE | 19907376 A1 | 8/2000 |
| EP | 1504749 A1 | 2/2005 |
| EP | 1935455 A1 | 6/2008 |
| EP | 2018841 A1 | 1/2009 |
| WO | 2012168060 A1 | 12/2012 |
| WO | 2013041485 A2 | 3/2013 |
| WO | 2013082413 A1 | 6/2013 |
| WO | 2014149019 A1 | 9/2014 |
| WO | 2016040158 A1 | 3/2016 |

* cited by examiner

*Primary Examiner* — Eisa B Elhilo
(74) *Attorney, Agent, or Firm* — Lorenz & Kopf, LLP

(57) ABSTRACT

The present disclosure concerns an agent for colouring keratinous fibres, in particular human hair, containing, in a cosmetic support,
(a) at least one direct dye,
(b) at least one amphoteric surfactant, in particular at least one alkylbetaine, and
(c) at least one alkylpolyglycoside, in particular at least one alkylpolyglucoside,
exemplified in that the content of amphoteric surfactant (b) in the agent—with respect to the total weight of the agent—is greater than the content of non-ionic surfactant (c). The present disclosure also concerns the use of the agent to colour keratinous fibres, as well as to a method in which the agent is applied to the keratinous fibres in order to colour them.

21 Claims, No Drawings

TONING SHAMPOO WITH IMPROVED COLOUR PERFORMANCE

CROSS-REFERENCE TO RELATED APPLICATION

This application claims priority to German Patent Application No. 10 2017 223 419.9, filed Dec. 20, 2017, which is incorporated herein by reference in its entirety.

TECHNICAL FIELD

The present disclosure pertains to the field of cosmetics and relates to agents for colouring (hereinafter also referred to as colorants) keratinous fibres, in particular human hair, which contain, in a cosmetic support, at least one direct dye as well as a combination of at least one amphoteric surfactant and at least one alkylpolyglycoside. These colorants are particularly suitable for:

increasing the chromaticity of dyes on keratinous fibres and/or increasing the colour uptake of dyes onto keratinous fibres and/or increasing the colour intensity of dyes on keratinous fibres.

In a second aspect, the present disclosure pertains to a method for colouring keratinous fibres, in which a colorant containing a combination of at least one amphoteric surfactant and at least one alkylpolyglycoside is employed.

In a third aspect, the present disclosure pertains to the use of the agent as contemplated herein for colouring keratinous fibres, in which a colorant containing a combination of at least one amphoteric surfactant and at least one alkylpolyglycoside is employed.

BACKGROUND

Changing the shape and colour of keratinous fibres, in particular hair, constitutes an important area of modern cosmetics. By employing this, the appearance of the hair as well as the latest fashion trends and also an individual's aspirations can be harmonized. In order to change the hair colour, the person skilled in the art will be aware of a variety of colouring systems which will satisfy the various requirements. For permanent, intense colours with good colour fastness and good grey coverage, oxidative dyes are usually used. Colorants of this type usually contain oxidative dye precursors, known as developer components and coupler components, which together produce the actual dyes under the influence of oxidizing agents such as hydrogen peroxide, for example. Oxidative dyes are distinguished by outstanding, long-lasting colour results, but on the downside are linked to a certain amount of damage to the hair.

If the consumer wishes to reduce damage to the hair or only to change the hair colour temporarily, then they may wish to turn to colorants which are based on direct dyes. Here, fully-formed dyes diffuse out of the colorant into the hair fibres. Compared with oxidative hair colouring, the colours obtained with direct dyes are less long-lasting and wash out more quickly. In addition, the grey coverage which can be obtained with direct dyes is generally in need of improvement. However, the advantage is that colouring with direct dyes causes less damage to the hair.

The person skilled in the art will divide direct dyes into various dye classes as a function of the desired colour result. The direct dyes which are known in the art belong, for example, to the nitro dye, anthraquinone dye, azo dye, triarylmethane dye or methine dye categories. All of these categories of dyes are intended to satisfy a specific set of requirements for use in the cosmetics arena. Thus, direct dyes deliver an intense colour result and superlative colour fastness. Environmental influences should affect the colour result obtained with direct dyes to the least extent possible, i.e. the dyes should, for example, possess good fastness to washing, light and rubbing. The influence of chemicals to which the keratinous fibres could be exposed following the colour process (for example permanent waving), should also change the colour result to the least possible extent.

Direct dyes can be divided into anionic, cationic and non-ionic direct dyes. In cosmetic compositions, these interact to varying degrees with the remaining components of the compositions. In this regard, surface-active substances such as surfactants or emulsifying agents which are contained in them have a major influence. In the cosmetic compositions, they are meant to release contaminants from the keratinous fibres and/or to emulsify components of the composition itself. However, depending on the choice of the surface-active substance, this may also lead to interactions between them and the direct dyes, whereupon the colour result could be significantly impaired compared with agents which contain no surface-active substances.

Surfactants or emulsifying agents are amphiphilic (bifunctional) compounds which include at least one hydrophobic and at least one hydrophilic portion of the molecule. The hydrophobic residue is usually a hydrocarbon chain. The hydrophilic residue may have a negative charge, a positive charge, a negative and a positive charge or no charge, depending on the type of surfactant.

In anionic surfactants, the hydrophilic portion of the molecule comprises at least one hydrophilic head group with a negative charge. Anionic surfactants exclusively contain negative charges. "Cationic surfactants" should be understood to mean surfactants, i.e. surface-active substances, which respectively have one or more positive charges. Cationic surfactants exclusively contain positive charges.

Zwitterionic (amphoteric) surfactants comprise, in the hydrophilic portion of the molecule, at least one group with a negative charge and at least one group with a positive charge. These are spatially separated from each other and are close to each other, whereupon the surfactant is electrically neutral overall.

Moreover, non-ionic (non-ionogenic) surfactants exist which are distinguished by the absence of electric charges in the molecules.

The person skilled in the art has long been aware that many surfactants can significantly impair the colour uptake of direct dyes onto keratinous fibres. Not all types of surfactants are compatible with all types of direct dyes. The colour uptake of direct dyes is to a large extent dependent on the type of surfactants and the type of the dyes. Anionic surfactants in this regard have a particular negative effect on the colour uptake of non-ionic and cationic dyes, as well as on anionic dyes. Cationic surfactants, on the other hand, have a particular negative impact on the colour uptake of non-ionic and anionic dyes, as well as on cationic dyes.

In order to overcome this problem, until now, as a rule, only compositions in which the dye and the surfactant have been precisely matched to each other are used. It is thus not possible to use any dye with any surfactant or to combine several dyes together in any manner in order to obtain the desired shade.

Correspondingly, the prior art discloses various such compositions. EP 1 935 455 A1 discloses a composition comprising a direct dye in combination with at least one bioheteropolysaccharide, at least one cationic surfactant and at least one amphoteric surfactant. WO 2013/041485 A2 describes a composition comprising at least one dye, for example a direct dye, at least one fat in the form of a long-chain dialkylcarbonate or dialkenylcarbonate, at least one alkylpolyglycoside as well as at least one cationic and/or amphoteric polymer. Examples of cleaning compositions with various combinations of surfactants are provided in WO 2016/040158 A1, WO 2013/082413 A1 and WO 2014/149019 A1. None of those compositions is particularly suitable for improving the colour distribution of direct dyes.

Conventional surfactant-containing colorants with direct dyes (toning shampoos) are usually optimized for either the best colouring properties or for the best cleaning properties or for the best foam formation. The range of mutually combinable direct colours and surfactants is limited, and so the flexibility of possible dye combinations with direct dyes is limited.

Thus, the objective of the present disclosure is to provide a surfactant-containing colorant based on direct dyes which is compatible with a wide variety of different direct dyes and which ensures good colour uptake. Furthermore, the agent should allow for as varied a range of colours, chromaticity and colour intensity as possible.

Finally, the agent should also exhibit good cleaning action and good foam formation properties and be easy to use.

BRIEF SUMMARY

Patent Claims Agents and methods for colouring keratinous fibres are provided herein. In an embodiment, an agent for colouring keratinous fibres includes, in a cosmetic support, (a) at least one direct dye, (b) at least one amphoteric surfactant, and (c) at least one alkylpolyglycosides. The total content of amphoteric surfactant (b) in the agent—with respect to the weight of the agent—is greater than the total content of alkylpolyglycoside (c).

In another embodiment, an agent for colouring keratinous fibres includes, in a cosmetic support, (a) at least one direct dye, (b) at least one amphoteric surfactant, and (c) at least one alkylpolyglycosides. The at least one direct dye (a) is present in a total quantity of from about 0.001 to about 7% by weight. The at least one amphoteric surfactant (b) is present in a total quantity of from about 0.5 to about 20.0% by weight, with respect to the weight of the agent. The at least one alkylpolyglycoside (c) is present in a total quantity of from about 0.5 to about 14.5% by weight, with respect to the weight of the agent. The total content of amphoteric surfactant (b) in the agent—with respect to the weight of the agent—is greater than the total content of alkylpolyglycoside (c). The total content of amphoteric surfactant (b) and alkylpolyglycoside (c) together amounts to from about 1.5 to about 20.0% by weight, with respect to the total weight of the agent.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

Surprisingly, it has now been shown that many different direct dyes can be used in a surfactant-containing cosmetic composition, in particular a shampoo (toning shampoo), with improved colouring performance, individually or in fact in combination with each other, when the surfactant-containing cosmetic composition comprises the at least one direct dye in combination with at least one amphoteric surfactant and at least one alkylpolyglycoside.

A particularly good colour uptake can be obtained when the content with respect to weight of amphoteric surfactant is greater than the content with respect to weight of alkylpolyglycoside. Further improvements in the colour uptake could be observed when the surfactant-containing formulation was produced using sodium chloride-free surfactant preparations.

In a first aspect, the present disclosure provides an agent for colouring keratinous fibres, in particular human hair, containing, in a cosmetic support,
(a) at least one direct dye,
(b) at least one amphoteric surfactant, in particular at least one alkylbetaine, and
(c) at least one alkylpolyglycoside, in particular at least one alkylpolyglucoside,
exemplified in that the total content with respect to weight of amphoteric surfactant (b) in the agent—with respect to the weight of the agent—is greater than the total content with respect to weight of alkylpolyglycoside (c).

The term "keratinous fibres" and also "keratin fibres" should be understood herein to mean fur, wool, feathers and in particular human hair. Although the agents are primarily suitable for colouring keratin fibres, in principle they can also be used in other arenas.

The term "agent for colouring" keratin fibres should be understood to mean colorants based on direct dyes which colour the keratin fibres.

An exemplifying feature of the agent as contemplated herein is its essential ingredients (b) and (c) content. It has been shown that particularly advantageous agents can be obtained when the total content with respect to weight of amphoteric surfactant (b) in the agent—with respect to the weight of the agent—is greater than the total content with respect to weight of alkylpolyglycoside (c).

The agent as contemplated herein contains at least one direct dye (a) as the first essential ingredient.

The direct dye or dyes (a) is or are preferably present in a total quantity of from about 0.001 to about 7% by weight, preferably of from about 0.01 to about 5.5% by weight, more preferably of from about 0.08 to about 3.4% by weight, more preferably of from about 0.1 to about 2% by weight, more preferably of from about 0.3 to about 1.5% by weight and particularly preferably of from about 0.6 to about 1% by weight, respectively with respect to the weight of the colorant.

Direct dyes (a) can be classified into anionic, cationic and non-ionic direct dyes. The direct dyes are usually selected from nitrophenylenediamines, nitroaminophenols, azo dyes, anthraquinones, triarylmethane dyes or indophenols and their physiologically acceptable salts.

In dyes which exclusively carry anionic charges, the person skilled in the art uses the term "acid dyes". The terms "anionic dye" and "acid dye" are therefore used synonymously in the context of the present disclosure. The term "anionic dyes" or "acid dyes" should be understood to refer to direct dyes which possess at least one carboxylic acid group (—COOH) and/or at least one sulphonic acid group (—SO$_3$H). Depending on the pH, the protonated forms (—COOH, —SO$_3$H) of the carboxylic acid or sulphonic acid groups are in equilibrium with their deprotonated forms (—COO$^-$, —SO$_3^-$). As the pH drops, the proportion of protonated forms rises. If direct dyes are used in the form of their salts, then the carboxylic acid groups or sulphonic acid groups are in the deprotonated form, and in order to maintain electrical neutrality, they are neutralized with corresponding stoichiometric equivalents of cations (such as the Na cation or K cation). An anionic dye does not carry any cationic charges.

Examples of suitable acid dyes may be selected from one or more compounds in the following group: Acid Yellow 1 (D&C Yellow 7, Citronin A, Ext. D&C Yellow No. 7, Japan Yellow 403, CI 10316, COLIPA n° B001), Acid Yellow 3 (COLIPA n°: C 54, D&C Yellow N° 10, Quinoline Yellow, E104, Food Yellow 13), Acid Yellow 9 (CI 13015), Acid Yellow 17 (CI 18965), Acid Yellow 23 (COLIPA n° C 29, Covacap Jaune W 1100 (LCW), Sicovit Tartrazine 85 E 102 (BASF), Tartrazine, Food Yellow 4, Japan Yellow 4, FD&C Yellow No. 5), Acid Yellow 36 (CI 13065), Acid Yellow 121 (CI 18690), Acid Orange 6 (CI 14270), Acid Orange 7 (2-Naphthol orange, Orange II, CI 15510, D&C Orange 4, COLIPA n° C015), Acid Orange 10 (CI 16230; Orange G sodium salt), Acid Orange 11 (CI 45370), Acid Orange 15 (CI 50120), Acid Orange 20 (CI 14600), Acid Orange 24 (BROWN 1; CI 20170; KATSU201; no sodium salt; Brown No.201; RESORCIN BROWN; ACID ORANGE 24; Japan Brown 201; D & C Brown No.1), Acid Red 14 (CI14720), Acid Red 18 (E124, Red 18; CI 16255), Acid Red 27 (E 123, CI 16185, C-Rot 46, Echtrot D, FD&C Red Nr.2, Food Red 9, Naphtholrot S), Acid Red 33 (Red 33, Fuchsia Red, D&C Red 33, CI 17200), Acid Red 35 (CI CI18065), Acid Red 51 (CI 45430, Pyrosin B, Tetraiodfluorescein, Eosin J, Iodeosin), Acid Red 52 (CI 45100, Food Red 106, Solar Rhodamine B, Acid Rhodamine B, Red n° 106 Pontacyl Brilliant Pink), Acid Red 73 (CI 27290), Acid Red 87 (Eosin, CI 45380), Acid Red 92 (D&C Red; Red 104; AKA231; RED 28; SUREDYE; 11969 Red; PHLOXINE;CI 45405;CI 45410; EOSINE B); Acid Red 95 (CI 45425, Erythrosine, Simacid Erythrosine Y), Acid Red 184 (CI 15685), Acid Red 195; Pigment Red 57:1 (E180;D&CRED7; CI 15850; Rubine 4BN; CI 15850:1; PIGMENT RED 57; Litholrubine BK; LITHOLRUBINE RB; LITHOLRUBINE BCA; Lithol Rubine B); Acid Violet 43 (Jarocol Violet 43, Ext. D&C Violet n° 2, CI 60730, COLIPA n° C063), Acid Violet 49 (CI 42640), Acid Violet 50 (CI 50325), Acid Blue 1 (Patent Blue, CI 42045), Acid Blue 3 (Patent Blau V, CI 42051), Acid Blue 7 (CI 42080), Acid Blue 104 (CI 42735), Acid Blue 9 (E 133, Patentblau AE, Amidoblau AE, Erioglaucin A, CI 42090, CI Food Blue 2), Acid Blue 62 (CI 62045), Acid Blue 74 (E 132, CI 73015), Acid Blue 80 (CI 61585), Acid Green 3 (CI 42085, Foodgreenl), Acid Green 5 (CI 42095), Acid Green 9 (CI 42100), Acid Green 22 (CI 42170), Acid Green 25 (CI 61570, Japan Green 201, D&C Green No. 5), Acid Green 50 (Brillantsäuregrün BS, CI 44090, Acid Brilliant Green BS, E 142), Acid Black 1 (Black n° 401, Naphthalene Black 10B, Amido Black 10B, CI 20470, COLIPA n° B15), Acid Black 52 (CI 15711), Food Yellow 8 (CI 14270), Food Blue 5, D&C Yellow 8, D&C Green 5, D&C Orange 10, D&C Orange 11, D&C Red 21, D&C Red 27, D&C Red 33, D&C Brown 1, bromophenol blue and/or tetrabromophenol blue.

In a further particularly preferred embodiment, an agent as contemplated herein contains (a) at least one anionic direct dye from the group of Acid Yellow 1, Acid Yellow 3, Acid Yellow 9, Acid Yellow 17, Acid Yellow 23, Acid Yellow 36, Acid Yellow 121, Acid Orange 6, Acid Orange 7, Acid Orange 10, Acid Orange 11, Acid Orange 15, Acid Orange 20, Acid Orange 24, Acid Red 14, Acid Red 18, Acid Red 27, Acid Red 33, Acid Red 35, Acid Red 51, Acid Red 52, Acid Red 73, Acid Red 87, Acid Red 92, Acid Red 95, Acid Red 184, Acid Red 195, Acid Violet 43, Acid Violet 49, Acid Violet 50, Acid Blue 1, Acid Blue 3, Acid Blue 7, Acid Blue 104, Acid Blue 9, Acid Blue 62, Acid Blue 74, Acid Blue 80, Acid Green 3, Acid Green 5, Acid Green 9, Acid Green 22, Acid Green 25, Acid Green 50, Acid Black 1, Acid Black 52, Food Yellow 8, Food Blue 5, D&C Yellow 7, D&C Yellow 8, D&C Orange 4, D&C Green 5, D&C Orange 10, D&C Orange 11, D&C Red 21, D&C Red 27, D&C Red 33, D&C Violet 2 and D&C Brown 1.

An agent as contemplated herein that comprises at least one anionic direct dye (a) from the group Acid Orange 7, Acid Red 33, Acid Red 92; Acid Violet 43, Acid Blue 9, Acid Blue 62 and Acid Black 1 is more particularly preferred.

The anionic direct dye or dyes is or are preferably present in a total quantity of from about 0.001 to about 7% by weight, preferably of from about 0.01 to about 5.5% by weight, more preferably of from about 0.1 to about 3.4% by weight and particularly preferably of from about 0.3 to about 2% by weight, respectively with respect to the weight of the colorant.

Further preferred colorants as contemplated herein are exemplified in that they contain at least one cationic direct dye as the direct dye (a). Dyes which carry exclusively cationic charges are usually also known as basic dyes.

Examples of suitable basic (cationic) dyes that may be mentioned are: Basic Blue 6 (CI-No. 51.175), Basic Blue 7 (CI-No. 42.595) Basic Blue 9 (CI-No. 52.015), Basic Blue 26 (CI-No. 44.045), Basic Blue 41 (CI-No. 11.154), Basic Blue 99 (CI-No. 56.059), HC Blue 15, HC Blue 16 (Bluequat-Bromid), Cationic Blue 347, Basic Brown 4 (CI-No. 21.010), Basic Brown 16 (CI-No. 12.250), Basic Brown 17 (CI-No. 12.251), Natural Brown 7 (CI-No. 75.500), Basic Green 1 (CI-No. 42.040), Basic Red 2 (CI-No. 50.240), Basic Red 22 (CI-No. 11.055), Basic Red 51, Basic Red 76 (CI-No. 12.245), Basic Violet 1 (CI-No. 42.535), Basic Violet 2, Basic Violet 3 (CI-No. 42.555), Basic Violet 10 (CI-No. 45.170), Basic Violet 14 (CI-No. 42.510), Basic Yellow 57 (CI-No. 12.719), Basic Yellow 87 and Basic Orange 31, as well as combinations of said dyes.

One or more dyes from the group HC Blue 15, HC Blue 16 (Bluequat-Bromid), Cationic Blue 347, Basic Violet 2, Basic Red 51, Basic Red 76, Basic Yellow 57, Basic Yellow 87, Basic Orange 31, and Basic Brown 17 have been shown to be particularly suitable.

An agent as contemplated herein contains at least one cationic direct dye (a) from the group HC Blue 15, HC Blue 16, Basic Red 76, Basic Yellow 57, Basic Orange 31, and Basic Brown 17 is more particularly preferred.

The cationic direct dye or dyes (a) are preferably present in a total quantity of from about 0.001 to about 7% by weight, preferably of from about 0.01 to about 5.5% by weight, more preferably of from about 0.1 to about 3.4% by weight and particularly preferably of from about 0.3 to about 2% by weight, respectively with respect to the weight of the colorant.

Further preferred colorants as contemplated herein are exemplified in that they contain at least one non-ionic direct dye as the direct dye (a). This may, for example, be selected from the group HC Yellow 2, HC Yellow 4, HC Yellow 5, HC Yellow 6, HC Yellow 12, HC Orange 1, Disperse Orange 3, HC Red 1, HC Red 3, HC Red 7, HC Red 10, HC Red 11, HC Red 13, HC Red BN, HC Blue 2, HC Blue 11, HC Blue 12, HC Blue 15, Disperse Blue 3, HC Violet 1, Disperse Violet 1, Disperse Violet 4, Disperse Black 9,1,4-diamino-2-nitrobenzene, 2-amino-4-nitrophenol, 1,4-bis-(2-hydroxyethyl)-amino-2-nitrobenzene, 3-nitro-4-(2-hydroxyethyl) aminophenol, 2-(2-hydroxyethyl)amino-4,6-dinitrophenol, 4-[(2-hydroxyethyl)amino]-3-nitro-1-methylbenzene, 1-amino-4-(2-hydroxyethyl)amino-5-chloro-2-nitrobenzene, 4-amino-3-nitrophenol, 1-(2'-ureidoethyl)amino-4-nitrobenzene, 2-[(4-amino-2-nitrophenyl)amino]benzoic acid, 4-[(3-hydroxypropyl)amino]-3-nitrophenol, 4-nitrophenylenediamine, 6-nitro-1,2,3,4-tetrahydroquinoxaline, 2-hydroxy-1,4-naphthoquinone, picramic acid and salts thereof, N,N'-bis-(2-hydroxyethyl)-2-nitro-p-phenylenediamine, 2-amino-6-chloro-4-nitrophenol, 4-ethylamino-3-nitrobenzoic acid and 2-chloro-6-ethylamino-4-nitrophenol.

More particularly preferably, an agent as contemplated herein comprises at least one non-ionic direct dye (a) from the group HC Red 1, HC Red 3, HC Red 7, HC Red 13, HC Orange 1, HC Yellow 2, HC Yellow 13, HC Blue 2, HC Blue 11, HC Blue 12, HC Blue 14, HC Violet 2, Disperse Violet 1, 4[(3-hydroxypropyl)amino]-3-nitrophenol and 4-amino-3-nitrophenol.

The non-ionic direct dye or dyes (a) is or are preferably present in a total quantity of from about 0.001 to about 7% by weight, preferably of from about 0.01 to about 5.5% by weight, more preferably of from about 0.1 to about 3.4% by weight and particularly preferably of from about 0.3 to about 2% by weight, respectively with respect to the weight of the colorant.

The following preferred direct dyes (a) may be highlighted: Basic Red 76, HC Blue 16, Basic Yellow 57, 4-hydroxypropylamino-3-nitrophenol, HC Red 13, HC Red 3, HC Blue 12, HC Orange 1, HC Blue 16 (Bluequat-Bromid), HC Yellow 2, N,N'-bis-(2-hydroxyethyl)-2-nitro-p-phenylenediamine, 4-amino-3-nitrophenol, Ext. D&C Violet 2, HC Violet 2, Basic Brown 17, Basic Red 76 and Basic Yellow 57, as well as mixtures thereof. Basic Red 76, HC Blue 16, Basic Yellow 57, 4-hydroxypropylamino-3-nitrophenol, 4-amino-3-nitrophenol, HC Red 13, HC Violet 2, as well as mixtures thereof are highly preferred. HC Blue 16, Basic Violet 2, Basic Yellow 57, 4-hydroxypropylamino-3-nitrophenol, HC Red 13 and 4-amino-3-nitrophenol as well as mixtures thereof are particularly preferred.

In a preferred embodiment, the agent as contemplated herein comprises a combination of a plurality of direct dyes. By combining a plurality of direct dyes, nuances in the overall colour spectrum can be obtained. In this regard, both a plurality of purely anionic, purely cationic or purely non-ionic dyes may be combined together; combinations of anionic, cationic and/or non-ionic dyes may be used as well.

Examples of suitable dyes which may be combined together are selected from HC Red 3, HC Blue 12, HC Orange 1, HC Blue 16 (Bluequat-Bromid), HC Yellow 2, N,N'-bis-(2-hydroxyethyl)-2-nitro-p-phenylenediamine, Ext. D&C Violet 2, Basic Brown 17, Basic Red 76, and Basic Yellow 57.

In general, the statements provided above regarding the quantities of the anionic, cationic or non-ionic direct dyes to be used are also applicable mutatis mutandis to combinations of several direct dyes. Preferably, with mixtures of dyes as well, the cited quantities for the total quantities of direct dyes (a) to be used in the direct dyes will not be exceeded.

Furthermore, the agent as contemplated herein comprises at least two surfactants, namely at least one amphoteric surfactant (b) and at least one alkylpolyglycoside (c). In this regard, it has been shown that, in particular, very intense colour results may be obtained when the agent as contemplated herein, in addition to a direct dye, contains at least one amphoteric surfactant (b) as well as at least one alkylpolyglycoside (c), wherein the total content with respect to weight of amphoteric surfactant (b) in the agent—with respect to the weight of the agent—is greater than the total content with respect to weight of alkylpolyglycoside (c).

In general, the total quantity of surfactants in the agent as contemplated herein is preferably up to about 50% by weight, highly preferably from about 1 to about 40% by weight, still more preferably from about 5 to about 30% by weight, and extremely preferably from about 7 to about 12% by weight, respectively with respect to the weight of the agent.

In a preferred embodiment, the total content—with respect to the weight of the agent—of amphoteric surfactants (b) and alkylpolyglycosides (c) together is from about 1.0 to about 25.0% by weight, preferably from about 1.5 to about 20.0% by weight, highly preferably from about 5.0 to about 15% by weight, and particularly preferably from about 6.0 to about 11.0% by weight.

As already discussed above, particularly advantageous effects may be observed when the agent as contemplated herein, with respect to its weight, comprises less alkylpolyglycoside (c) than amphoteric surfactant (b). Preferably, the weight ratio of amphoteric surfactant to alkylpolyglycoside is in the range from about 1:0.9 to about 1:0.1, highly preferably in the range from about 1:0.3 to about 1:0.8 and in particular in the range from about 1:0.5 to about 1:0.7.

With respect to the total weight of the agent, the total quantity of at least one amphoteric surfactant (b) is preferably from about 0.5 to about 20.0% by weight, highly preferably from about 1.0 to about 14.5% by weight, particularly preferably from about 2.0 to about 9.5% by weight and in particular from about 3.0 to about 7.0% by weight.

With respect to the total weight of the agent, the total quantity of at least one alkypolyglycoside (c) is preferably from about 0.5 to about 14.5% by weight, highly preferably from about 1.0 to about 6.7% by weight, and in particular from about 1.5 to about 4.0% by weight.

In one embodiment, the agent comprises, with respect to its total weight, at least one amphoteric surfactant (b) in a total quantity of from about 0.5 to about 20.0% by weight and at least one alkylpolyglycoside (c) in a total quantity of from about 0.5 to about 14.5% by weight, with the proviso that the total content with respect to weight of amphoteric surfactant (b) in the agent—with respect to the weight of the agent—is greater than the total content with respect to weight of alkylpolyglycoside (c), wherein the weight ratio of amphoteric surfactant to alkylpolyglycoside is preferably in the range from about 1:0.9 to about 1:0.1, highly preferably in the range from about 1:0.3 to about 1:0.8 and in particular in the range from about 1:0.5 to about 1:0.7.

In a further embodiment, the agent comprises, with respect to its total weight, at least one amphoteric surfactant (b) in a total quantity of from about 1.0 to about 14.5% by weight and at least one alkylpolyglycoside (c) in a total quantity of from about 1.0 to about 6.7% by weight, with the proviso that the total content with respect to weight of amphoteric surfactant (b) in the agent—with respect to the weight of the agent—is greater than the total content with respect to weight of alkylpolyglycoside (c), wherein the weight ratio of amphoteric surfactant to alkylpolyglycoside is preferably in the range from about 1:0.9 to about 1:0.1, highly preferably in the range from about 1:0.3 to about 1:0.8 and in particular in the range from about 1:0.5 to about 1:0.7.

In a further embodiment, the agent comprises, with respect to its total weight, at least one amphoteric surfactant (b) in a total quantity of from about 2.0 to about 9.5% by weight, in particular from about 3.0 to about 7.0% by weight, and at least one alkylpolyglycoside (c) in a total quantity of from about 1.5 to about 4.0% by weight, with the proviso that the total content with respect to weight of amphoteric surfactant (b) in the agent—with respect to the weight of the agent—is greater than the total content with respect to weight of alkylpolyglycoside (c), wherein the weight ratio of amphoteric surfactant to alkylpolyglycoside is preferably in the range from about 1:0.9 to about 1:0.1, highly preferably in the range from about 1:0.3 to about 1:0.8 and in particular in the range from about 1:0.5 to about 1:0.7.

As already explained above, the hydrophilic portions of the molecules of the amphoteric surfactants (b) comprise a negatively charged and at least one positively charged group. Examples of preferred amphoteric surfactants (b) are betaines, N-alkyl-N,N-dimethylammonium glycinates, N-acylaminopropyl-N,N-dimethylammonium glycinates and 2-alkyl-3-carboxymethyl-3-hydroxyethyl imidazolines respectively containing from about 8 to about 24 carbon atoms in the alkyl group.

In a preferred embodiment, at least one betaine, in particular at least one alkylbetaine, is used as the amphoteric surfactant (b). Particularly preferably, it is an alkylamidoalkylbetaine with the following formula (I):

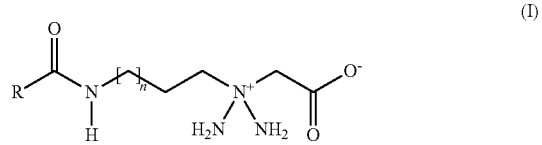

(I)

wherein

R represents a linear or branched, saturated or unsaturated hydrocarbon residue containing from about 5 to about 20, preferably from about 8 to about 14 carbon atoms, and n is a whole number from about 0 to about 10, in particular from about 0 to about 4.

In a preferred embodiment, R is a linear hydrocarbon residue, in particular a linear, saturated hydrocarbon residue.

In a more particularly preferred embodiment, an alkylamidoalkylbetaine with formula (I) is used in which R=—$C_{10}H21$, —$C_{11}H_{23}$ or —$C_{12}H_{25}$ and n=0, 1 or 2; in particular, an alkylamidoalkylbetaine with formula (I) in which R=—$C_{11}H_{23}$ and n=1 is used as the amphoteric surfactant (b), also known as cocamidopropylbetaine.

Preferably, the aqueous commercial product preparation of the amphoteric surfactant (b) is essentially free from sodium chloride, which means that it comprises <0.5% by weight, preferably <0.4% by weight, particularly preferably <0.2% by weight of sodium chloride, respectively with respect to the total weight of the aqueous commercial product preparation of the amphoteric surfactant (b).

Sodium chloride—depleted, high purity cocamidopropylbetaine with an active substance content of 35% by weight of cocamidopropylbetaine and a sodium chloride content of <0.5% by weight is obtainable, for example, under the trade names EMPIGEN® Total Active TC/U from the manufacturer Huntsman Corporation.

The alkylpolyglycosides (c) are non-ionic surfactants, which are exemplified by the absence of electric charges in the molecules.

Alkylpolyglycosides as contemplated herein are exemplified by the fact that they comprise a hydrophobic, long-chain alkyl residue and a glycoside sugar as the hydrophilic portion of the molecule. In a preferred embodiment, the alkylpolyglycoside comprises at least one linear, branched or cyclic, saturated or unsaturated alkyl residue containing from about 1 to about 30 carbon atoms, preferably from about 5 to about 25 carbon atoms and in particular from about 8 to about 20 carbon atoms. Particularly preferably, the alkyl residue is linear, and highly preferably, linear and saturated. The degree of polymerization of the glycoside sugar is preferably from about 1 to about 10, in particular from about 1 to about 5, particularly preferably from about 1.1 to about 2.

Particularly preferred alkylpolyglycosides are alkylpolyglucosides.

Particularly preferred alkylpolyglucosides include laurylpolyglucoside, decylpolyglucoside, octylpolyglucoside and cocoglucoside, in particular laurylpolyglucoside. Laurylpolyglucoside can be obtained, for example, under the trade name PLANTACARE® from BASF.

Particularly preferred alkylpolyglycosides include laurylpolyglycoside, decylpolyglycoside, octylpolyglycoside and cocoglycoside, in particular laurylpolyglycoside.

Preferably, the aqueous commercial product preparation of the alkylpolyglycoside is essentially free from sodium chloride, i.e. it comprises <0.5% by weight, preferably <0.4% by weight, particularly preferably <0.2% by weight of sodium chloride, respectively with respect to the total weight of the aqueous commercial product preparation of the alkylpolyglycoside (c). Laurylpolyglycoside can be obtained, for example, under the trade name PLANTACARE® from the manufacturer BASF SE.

In a particularly preferred embodiment, the colorant as contemplated herein is essentially free from sodium chloride, i.e. it comprises <0.2% by weight, in particular<0.1% by weight, still more preferably <0.05% by weight, particularly preferably <0.02% by weight, extremely preferably from about 0.005 to about 0.015% by weight of sodium chloride, more extremely preferably about 0% by weight of sodium chloride, respectively with respect to the total weight of the colorant.

In a particularly preferred embodiment of the present disclosure, in order to colour keratinous fibres, in particular human hair, the agent comprises, contained in a cosmetic support, (a) at least one direct dye, (b) at least one alkylamidoalkylbetaine with formula (I), preferably cocamidopropylbetaine ($C_{11}H_{23}$)C(O)NH($C_3H_6$)N($NH_2$)$_2$$CH_2$C(O)O, and (c) at least one alkylpolyglucoside, preferably laurylglycoside, with the proviso that the agent is essentially free from sodium chloride, exemplified in that the total content with respect to weight of amphoteric surfactant (b) in the agent—with respect to the weight of the agent—is greater than the total content with respect to weight of alkylpolyglycoside (c).

The treatment of keratinous fibres with agents which contain (a) at least one direct dye, (b) at least one amphoteric surfactant and (c) at least one alkylpolyglycoside, results in particularly intense colours in attractive nuances. In this regard, it has surprisingly been shown that the colour uptake properties could be optimized still further by using the combination of an amphoteric surfactant (b) and an alkylpolyglycoside (c) in a weight ratio of from about 1:0.9 to about 1:0.1, highly preferably in the range from about 1:0.3 to about 1:0.8 and in particular in the range from about 1:0.5 to about 1:0.7. Particularly intense colours were obtained when, in addition to the direct dyes (a), the colorants employed at least one amphoteric surfactant (b) from the alkylamidoalkylbetaines group and at least one alkylpolyglycoside (c) from the alkylpolyglucosides group.

In a particularly preferred embodiment, an agent as contemplated herein contains (b) at least one amphoteric surfactant, which is selected from the group formed by alkylamidoalkylbetaines with formula (I), in particular cocamidopropylbetaine, $((C_{11}H_{23})C(O)NH(C_3H_6)N(NH_2)_2CH_2C(O)O)$.

Furthermore, particularly good results are obtained when the aqueous commercial product preparations of surfactants (b) and (c) are essentially free from sodium chloride. The term "essentially free from sodium chloride" here means a sodium chloride content of <0.5% by weight, preferably <0.4% by weight, particularly preferably <0.2% by weight, respectively with respect to the total weight of the aqueous commercial product preparation of the amphoteric surfactant (b) or of the alkylpolyglycoside (c).

The colorants may furthermore contain additional substances, auxiliary substances and additives to improve the colour performance and to set up the other desired properties of the agent. Preferably, the colorants are provided as liquid preparations and the agents are thus optionally additionally supplemented with a further surface-active substance, wherein such surface-active substances are known as surfactants or emulsifying agents, depending on the sector of application. They are preferably selected from sulphate-free anionic, cationic, non-ionic, ampholytic and amphoteric surfactants and emulsifying agents.

As already discussed above, the term "cationic surfactants" should be understood to mean surfactants, i.e. surface-active compounds, respectively with one or more positive charges. Cationic surfactants contain exclusively positive charges. Usually, these surfactants are constructed from a hydrophobic portion and a hydrophilic head group, wherein the hydrophobic portion usually includes a hydrocarbon backbone (for example including one or two linear or branched alkyl chains), and the positive charge(s) are located in the hydrophilic head group. Cationic surfactants are adsorbed at interfaces and aggregate in aqueous solutions above the critical micelle formation concentration to form positively charged micelles.

Examples of cationic surfactants are:

quaternary ammonium compounds which may carry one or two alkyl chains with a chain length of from about 8 to about 28 C atoms, quaternary phosphonium salts, substituted with one or more alkyl chains with a chain length of from about 8 to about 28 C atoms, or tertiary sulphonium salts.

Furthermore, the cationic charge may also be in the form of an onium structure as a component of a heterocyclic ring (for example an imidazolium ring or a pyridinium ring). In addition to the functional unit, which carries the cationic charge, the cationic surfactant may also contain other uncharged function groups; this is the case with esterquats, for example. Examples of cationic surfactants of this type are the physiologically acceptable salts of N,N,N-trimethyl-1-hexadecanaminium, in particular N,N,N-trimethyl-1-hexadecanaminium chloride, which is also marketed under the trade name Dehyquart A-CA. A further suitable cationic surfactant is a physiologically acceptable salt of dimethyldistearyldimethylammonium, particularly preferably dimethyldistearylammonium chloride. Further cationic surfactants may be selected from the group formed by cationic imadazolium compounds.

Examples of preferred ampholytic surfactants are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids, wherein the ampholytic surfactant is different from the amphoteric surfactant (b).

The one or more amphotytic and/or cationic surfactants may be present in a total quantity of from about 0.0 to about 5.0% by weight, preferably of from about 0.1 to about 2.5% by weight, more preferably of from about 0.4 to about 1.8% by weight and particularly preferably of from about 0.6 to about 0.9% by weight—respectively with respect to the total weight of the agent.

In anionic surfactants, the hydrophilic portion of the molecule comprises a negatively charged hydrophilic head group. The negatively charged hydrophilic head group may, for example, be a carboxylic acid group or the salt of a carboxylic acid group, a sulphonic acid group or the salt of the sulphonic acid group, a sulphuric acid ester group or the salt thereof, a phosphonic acid group or the salt of the phosphonic acid group, or a phosphoric acid ester group or the salt thereof.

Usually, the cosmetic agent as contemplated herein comprises an aqueous support. In aqueous solution, the aforementioned hydrophilic head groups of the anionic surfactant—such as, for example, the carboxylic acid and the salts of the carboxylic acids—are in equilibrium, the position of which being determined by the pH of the agent. Thus, if a fatty acid is used as the anionic surfactant, then a small portion of the fatty acid is present in aqueous solution in the form of the protonated fatty acid, whereas the major portion of the fatty acid is deprotonated in aqueous solution and in this manner, is transformed into the salt of the fatty acid. For this reason, the definition of an anionic surfactant also encompasses a surfactant with a—highly protonated—acid group. In the context of the present disclosure, an "anionic surfactant" does not contain any cationic groups, i.e. amphoteric surfactants are not included in the definition of an anionic surfactant.

Thus, anionic surfactants are exemplified by the presence of an anionic group which renders it water-soluble, such as, for example, a carboxylate, sulphate, sulphonate or phosphate group and a lipophilic alkyl group containing approximately 8 to about 30 C atoms. In addition, the molecule may contain glycol or polyglycol ether groups, ester, ether and amide groups as well as hydroxyl groups.

Typical examples of anionic surfactants are alkylbenzenesulphonates, alkanesulphonates, olefinsulphonates, alkylethersulphonates, glycerin ethersulphonates, α-methylestersulphonates, sulphofatty acids, alkylsulphates, fatty alcohol ether sulphates, glycerin ethersulphates, hydroxy mixed ether sulphates, monoglyceride(ether)sulphates, fatty acid amide(ether)sulphates, mono- and dialkylsulphosuccinates, mono- and dialkylsulphosuccinamates, sulphotriglycerides, amide soaps, ethercarboxylic acids and salts thereof, fatty acid isethionates, fatty acid sarcosinates, fatty acid taurides, acyl lactylates, acyl tartrates, acyl glutamates, acyl aspartates, alkyloligoglucoside sulphates, protein fatty acid condensates (in particular wheat-based plant products) and alkyl(ether)phosphates. Insofar as the anionic surfactants may contain polyglycolether chains, these may have a conventional distribution of homologues, but preferably a narrow distribution thereof.

Anionic surfactants, in particular sulphated surfactants, i.e. anionic surfactants, comprising at least one sulphate group ($-OSO_3$), as a rule have a negative influence on the colour uptake of direct dyes, in particular cationic direct dyes. In a particularly preferred embodiment, the agent as contemplated herein thus comprises only small quantities of surfactants which comprise sulphate groups, in particular alkyl sulphates and alkyl ethersulphates such as fatty alcohol ether sulphates, glycerin ether sulphates, hydroxy mixed ether sulphates, monoglyceride(ether) sulphates, fatty acid amide (ether) sulphates. Preferably, the agent comprises sulphate group-containing surfactants in a total quantity of from about 0 to ≤0.2% by weight, preferably of from about 0 to ≤0.15% by weight and in particular from about 0 to ≤0.1% by weight, with respect to the total weight of the agent. More particularly preferably, the agent is free from surfactants containing sulphate groups.

In a further, particularly preferred embodiment, the agent as contemplated herein comprises only small quantities of anionic surfactants. Preferably, the agent as contemplated herein comprises anionic surfactants in a total quantity of from about 0 to ≤0.2% by weight, more preferably of from about 0 to ≤0.15% by weight, and in particular of from about 0 to ≤0.1% by weight, with respect to the total weight of the agent. More particularly preferably, the agent is free from anionic surfactants.

In a further, particularly preferred embodiment, the agent as contemplated herein exclusively comprises, as the surfactant, the at least one amphoteric surfactant (b) in combination with the at least one alkylpolyglycoside (c).

The ready-to-use agents may contain further auxiliary substances and additives. Colouring processes on keratinous fibres are usually carried out in the weakly acidic to alkaline range, preferably in the weakly acidic to weakly alkaline medium. In order to care for the keratinous fibres as well as the skin as much as possible, however, it is not desirable to set the pH too high.

In principle, the pH of the agent may be in the range from about pH 2 to about pH 11, preferably in the range from about pH 3 to about pH 8. In a further more particularly preferred embodiment, an agent as contemplated herein has a pH in the range from about 2 to about 11, preferably from about 3 to about pH 8, particularly preferably from about 3.5 to about 7.0, more preferably from about 4.0 to about 6.5 and more particularly preferably from about 4.5 to about 5.5.

The pH may, for example, be measured using a glass electrode, which is usually in the form of a combination electrode. The pHs of the present disclosure are pHs which are measured at a temperature of 22° C.

The alkalisation agent which may be used to set the preferred pH may be selected from the group formed by ammonia, alkanolamines, basic amino acids, as well as inorganic alkalisation agents such as alkali (alkaline-earth) metal hydroxides, alkali (alkaline-earth) metal metasilicates, alkali (alkaline-earth) metal phosphates and alkali (alkaline-earth) metal hydrogen phosphates. Preferred inorganic alkalisation agents are magnesium carbonate, sodium hydroxide, potassium hydroxide, sodium silicate and sodium metasilicate. Organic alkalisation agents which may be used as contemplated herein are preferably selected from monoethanolamine, 2-amino-2-methylpropanol and triethanolamine. The basic amino acids which may be used as alkalisation agents as contemplated herein are preferably selected from the group formed by arginine, lysine, ornithine and histidine, particularly preferably arginine. However, in the context of experiments in connection with the present disclosure, it has been shown that further agents as contemplated herein are exemplified in that they additionally contain an organic alkalisation agent. One embodiment of the first aspect of the present disclosure is exemplified in that the agent additionally contains at least one alkalisation agent which is selected from the group formed by ammonia, alkanolamines and basic amino acids, in particular from ammonia, monoethanolamine and arginine or one of its acceptable salts.

Acidification agents which may be used to adjust the pH are organic acids such as citric acid, acetic acid, ascorbic acid, benzoic acid, lactic acid, malic acid and maleic acid, as well as mineral salts such as hydrochloric acid, sulphuric acid or phosphoric acid.

Furthermore, it has been shown to be advantageous for the colorant to contain at least one stabilizer or chelating agent. Particularly preferred stabilizers are phenacetin, alkalibenzoates (sodium benzoate) and salicylic acid. Furthermore, any of the prior art chelating agents may be used. Preferred chelating agents as contemplated herein are nitrogen-containing polycarboxylic acids, in particular EDTA and EDDS, and phosphonates, in particular 1-hydroxyethane-1,1-diphosphonate (HEDP) and/or ethylenediamine tetramethylene phosphonate (EDTMP) and/or diethylenetriamine pentamethylene phosphonate (DTPMP) or sodium salts thereof.

Furthermore, the agents as contemplated herein may contain other substances, auxiliary substances and additives such as, for example, non-ionic polymers such as, for example, vinylpyrrolidinone/vinylacrylate copolymers, polyvinylpyrrolidinone, vinylpyrrolidinone/vinylacetate copolymers, polyethylene glycols and polysiloxanes; silicones such as volatile or non-volatile, straight-chained, branched or cyclic, crosslinked or non-crosslinked polyalkylsiloxanes (such as dimethicones or cyclomethicones), polyarylsiloxanes and/or polyalkylarylsiloxanes, in particular polysiloxanes with organofunctional groups, such as substituted or unsubstituted amines (amodimethicones), carboxyl-, alkoxy- and/or hydroxyl groups (dimethicone copolyols), linear polysiloxane A)-polyoxyalkylene B) block copolymers, graft silicone polymers; cationic polymers such as quaternized cellulose ethers, polysiloxanes with quaternary groups, dimethyldiallylammonium chloride polymers, acrylamide-dimethyldiallylammonium chloride copolymers, dimethylaminoethylmethacrylate-vinylpyrrolidinone copolymers quaternized with diethylsulphate, vinylpyrrolidinone-imidazolinium methochloride copolymers and quaternized polyvinylalcohol; zwitterionic and amphoteric polymers; anionic polymers such as, for example, polyacrylic acids or crosslinked polyacrylic acids; fats such as, for example, $C_8$-$C_{30}$ fatty alcohols, hydrocarbons or natural oils and fats; hair conditioning compounds such as phospholipids, for example lecithin and cephalins; perfume oils, dimethylisosorbide and cyclodextrin; fibre structure-improving substances, in particular mono-, di- and oligosaccharides such as, for example, glucose, galactose, fructose, fruit sugar and lactose; colorants to colour the agent; antidandruff substances such as piroctone olamine, zinc omadine and climbazole; amino acids and oligopeptides; animal and/or plant-based protein hydrolysates, also in the form of their fatty acid condensation products or possibly anionically or cationically-modified derivatives; light stabilizers and UV screens; substances such as panthenol, pantothenic acid, pantolactone, allantoin, pyrrolidinone carboxylic acids and salts thereof as well as bisabolol; polyphenols, in particular hydroxycinnamic acids, 6,7-dihydroxycoumarins, hydroxybenzoic acids, catechins, tannins, leukoanthocyanidines, anthocyanidines, flavanones, flavones and flavonols; ceramides or pseudoceramides; vitamins, provitamins and vitamin precursors; plant extracts; fats and waxes such as fatty alcohols, beeswax, montan wax and paraffins; swelling and penetration substances such as glycerin, propylene glycol monoethylether, carbonates, hydrogen carbonates, guanidines, ureas as well as primary, secondary and tertiary phosphates; opacifiers such as latex, styrene/PVP and styrene/acrylamide copolymers; pearlizing agents such as ethylene glycol mono- and di-stearate, as well as PEG-3 distearate and pigments.

The person skilled in the art will be able to select these further substances in accordance with the desired properties of the agent. Regarding further optional components as well as the quantities of these components which are used, reference should expressly be made to the relevant handbooks known to the person skilled in the art. The additional substances and auxiliary substances are preferably present in the agents as contemplated herein in respective quantities of from about 0.0001 to about 25% by weight, in particular from about 0.0005 to about 15% by weight, with respect to the total weight of the respective agent.

The agents as contemplated herein contain the direct dyes in combination with at least one amphoteric surfactant (b) and at least one alkylpolyglycoside (c) in a cosmetic support. This cosmetic support is preferably aqueous, alcoholic or aqueous alcoholic. For the purposes of hair treatment, examples of such supports are creams, emulsions, gels or in fact surfactant-containing foaming solutions, such as shampoos, foam aerosols or other preparations, for example, which are suitable or application to the hair. Shampoos (toning shampoos) are particularly suitable.

An aqueous support in the context of the present disclosure contains at least about 40% by weight, in particular about 50% by weight of water. The term "aqueous alcoholic supports" as used in the context of the present disclosure should be understood to mean water-containing compositions containing from about 3 to about 70% by weight of a $C_1$-$C_4$-alcohol, in particular ethanol or isopropanol. The agents as contemplated herein may additionally contain further organic solvents such as, for example, 4-methoxybutanol, ethyldiglycol, 1,2-propyleneglycol, n-propanol, n-butanol, 1,3-butyleneglycol, glycerin, diethylene glycol monoethylether, and diethylene glycol mono-n-butylether. In this regard, any water-soluble organic solvent is preferred. Preferred agents as contemplated herein are exemplified in that they additionally contain a non-aqueous solvent, wherein preferred agents as contemplated herein preferably contain the solvent in a concentration of from about 0.1 to about 20% by weight, preferably in a concentration of from about 0.5 to about 10% by weight, more particularly preferably in a concentration of from about 1 to about 7% by weight, respectively with respect to the total weight of the agent. It has been shown that the combination as contemplated herein of at least one amphoteric surfactant and at least one alkylpolyglycoside increases the solubility of the direct dyes, so that the quantity of solvents, in particular of 1,2-propyleneglycol and 1,3-butyleneglycol, can be reduced. Frequently, only from about 1 to about 5% by weight of these solvents is required in the colorants as contemplated herein.

Furthermore, at least one penetration enhancer may also be present. As a rule, penetration enhancers can also act as a solvent.

Examples of suitable penetration enhancers that may be mentioned in this regard are propylene carbonate, benzyl alcohol, 2-phenoxyethan-1-ol and/or benzyl alcohol.

In a far more particularly preferred embodiment, an agent as contemplated herein additionally contains at least one penetration enhancer from the group formed by propylene carbonate, benzyl alcohol, 2-phenoxyethan-1-ol and/or benzyl alcohol.

It is of greater advantage when the colorant as contemplated herein contains at least one penetration enhancer from the group formed by benzyl alcohol, 2-phenoxyethan-1-ol and/or propylene carbonate. Using one or more solvents from this group means that the colour uptake of the acid dyes can be reinforced disproportionately. Furthermore, it has been shown that the fastness properties of the colours that can be obtained with the agent as contemplated herein are better.

If keratinous fibres are coloured with an agent containing at least one of the two aromatic alcohols, then upon subsequent colouring with direct acid dyes, colours may be obtained which are exemplified by very good grey coverage. In addition, the fastness to washing of these colours is outstanding.

The agent as contemplated herein may preferably contain the solvent or solvents in specific total quantities in the range from about 0 to about 20.0% by weight, preferably from about 1.0 to about 17.0% by weight, more preferably from about 5.0 to about 14.0% by weight and more particularly preferably from about 8.5 to about 12.5% by weight. All of the quantities are given with respect to the total quantity of all of the solvents present in the agent, which are in relation to the total weight of the agent.

The agent as contemplated herein furthermore contains additional substances, auxiliary substances and additives for improving the colour performance and other desirable properties of the agent. As already discussed, the agent is preferably provided as a liquid preparation. It has been shown to be advantageous for the agent to contain at least one thickening agent. In principle, there are no limitations as regards the nature of this thickening agent. It may be both an organic and also purely inorganic thickening agent. Suitable thickening agents are anionic, synthetic polymers; cationic, synthetic polymers, naturally occurring thickening agents such as non-ionic guar gums, scleroglucan gums or xanthan gums, gum arabicum, ghatti gum, karaya gum, tragacanth gum, carrageenan gum, agar-agar, carob bean gum, pectins, alginates, starch fractions and derivatives such as amylose, amylopectin and dextrins, as well as cellulose derivatives such as, for example, methylcellulose, carboxyalkylcelluloses and hydroxyalkylcelluloses; non-ionic, fully synthetic polymers such as polyvinylalcohol or polyvinylpyrrolidinone; as well as inorganic thickening agent, in particular phyllosilicates such as, for example, bentonite, in particular smectite, such as montmorillonite or hectorite.

Thickening agents with an associative action (associative thickening agents) are particularly preferred, such as hydrophobically modified polyacrylates (HASE), hydrophobically modified cellulose ethers (HMHEC), hydrophobically modified polyacrylamides (HMPAM), hydrophobically modified polyethers (HMPE) as well as associative polyurethane thickening agents. Hydrophobically modified cellulose ethers, in particular $C_5$-$C_{25}$-alkylhydroxyethylcellulose, preferably $C_{10}$-$C_{20}$-alkylhydroxyethylcellulose, for example $C_{14}$-alkylhydroxyethylcellulose, $C_{15}$-alkylhydroxyethylcellulose, $C_{16}$-alkylhydroxyethylcellulose, $C_{17}$-alkylhydroxyethylcellulose, $C_{18}$-alkylhydroxyethylcellulose, as well as mixtures thereof, are particularly preferred.

Cetylhydroxyethylcellulose, obtainable under the trade name Natrosol™ Plus 330 CS from Ashland, is particularly preferred.

Preferably, the at least one thickening agent is present in a total quantity of from about 0.1 to about 5% by weight, particularly preferably from about 0.1 to about 3% by weight, highly preferably from about 0.1 to about 2% by weight, still more preferably from about 0.2 to about 1.5% by weight and in particular from about 0.5 to about 1% by weight, respectively with respect to the weight of the agent.

The agent as contemplated herein may also contain anionic polymeric thickening agents. Examples of suitable compounds are selected from crosslinked or non-crosslinked copolymers which contain at least two different monomers from the group formed by acrylic acid, methacrylic acid, $C_1$-$C_6$-alkyl esters of acrylic acid and/or $C_1$-$C_6$-alkyl esters of methacrylic acid. Particularly preferred anionic copolymers are copolymers of acrylic acid, methacrylic acid or their $C_1$-$C_6$-alkyl esters, which are marketed under the INCI name acrylates copolymer. The combination of methacrylic acid and ethyl acrylate as well as optionally crosslinked, multifunctional monomers is particularly preferred. An example of a preferred commercial product in this regard is Aculyn® 33 or 33A, supplied by Rohm & Haas. A further preferred anionic polymeric thickening agent is polyacrylate-1 crosspolymer, a copolymer of at least one $C_1$-$C_6$-alkyl ester of acrylic acid or methacrylic acid, C1-4 dialkylamino-C1-6 alkylmethacrylate, PEG/PPG-30/5 allylether, PEG-20-25-C10-30 alkylethermethacrylate and hydroxy-C2-6 alkylmethacrylate, which is crosslinked with ethylene glycol dimethacrylate.

Furthermore, the agent as contemplated herein may contain, as a film-forming agent, one or more cationic compounds from the group polyquaternium-1, polyquaternium-2, polyquaternium-3, polyquaternium-4, polyquaternium-5, polyquaternium-6, polyquaternium-7, polyquaternium-8, polyquaternium-9, polyquaternium-10, polyquaternium-11, polyquaternium-14, polyquaternium-16, polyquaternium-17, polyquaternium-18, polyquaternium-22, polyquaternium-24, polyquaternium-27, polyquaternium-28, polyquaternium-32, polyquaternium-33, polyquaternium-37, polyquaternium-39, polyquaternium-44, polyquaternium-46, polyquaternium-53, polyquaternium-55, polyquaternium-64, polyquaternium-67, polyquaternium-68, polyquaternium-69 and/or polyquaternium-86 as a film-forming agent.

Polyquaternium-37 may be highlighted as a particularly preferred film-forming agent. This improves the properties of the agent and the quality of the colour that is obtained.

Preferably, a cationic polyquaternium compound is present in a total quantity of from about 0.1 to about 5% by weight, particularly preferably from about 0.2 to about 3% by weight, highly preferably from about 0.3 to about 2% by weight and in particular in a quantity of from about 0.5 to about 1% by weight, respectively with respect to the weight of the agent.

Preferably, at least one associative thickening agent, in particular a hydrophobically modified cellulose ether, and at least one polyquaternium compound are used in combination with each other. Particularly good colour results could be obtained with a combination of cetylhydroxyethylcellulose and polyquaternium-37.

Furthermore, hair conditioning compounds may advantageously be contained in the agents. Hair conditioning compounds endow human hair with substantivity because, for example, of cationic groups or groups which can form cations, in particular protonated amino groups of quaternary ammonium group. Particularly preferred hair conditioning compounds are cationic and/or amphoteric polymers.

The agent as contemplated herein can be formulated in a variety of forms. Thus, for example, it may be applied as a gel, as an emulsion, as a solution or even in the form of a colouring mousse. The use of gels (shampoo) constitutes a particularly attractive and comfortable form of application for the consumer and is therefore preferred. The gel may be applied directly to the keratinous fibres to be coloured and the application procedure can be integrated seamlessly into the daily hygiene routine of the consumer. Thus, particularly preferably, the agent is formulated as a shampoo (toning shampoo).

In one aspect, the present disclosure thus also provides an agent for colouring keratinous fibres, in particular human hair, containing, in a cosmetic support in the form of a shampoo,
(a) at least one direct dye,
(b) at least one amphoteric surfactant, in particular at least one alkylbetaine,
(c) at least one alkylpolyglycoside, in particular at least one alkylpolyglucoside,
(d) water, and
(e) at least one thickening agent,
preferably with the proviso that the agent is essentially free from sodium chloride,
exemplified in that the content of amphoteric surfactant (b) in the agent is greater than the content of non-ionic surfactant (c).

In a further aspect, the present disclosure also provides an agent for colouring keratinous fibres, in particular human hair, containing, in a cosmetic support in the form of a shampoo,
(a) at least one direct dye,
(b) at least one amphoteric surfactant, in particular at least one alkylbetaine,
(c) at least one alkylpolyglycoside, in particular at least one alkylpolyglucoside,
(d) water,
(e) at least one thickening agent, and
(f) at least one film-forming agent,
preferably with the proviso that the agent is essentially free from sodium chloride,
exemplified in that the content of amphoteric surfactant (b) in the agent is greater than the content of non-ionic surfactant (c).

The agents may be formulated as a single-component agent or as a multi-component agent such as a two-component agent or a three-component agent and be used accordingly. Separation into multi-component systems is particularly appropriate in cases where incompatibilities between the ingredients are anticipated or suspected; the agent to be used in such systems is produced by the consumer directly prior to application by mixing the components. Preferably, the agent as contemplated herein is formulated as a single-component agent.

The term "agent for colouring keratinous fibres" should always be understood to mean the ready-to-use agent. If the agent is supplied to the consumer in the form of a single-component agent, then the ready-to-use agent does not have to be made up first, but can be taken directly from the container in which it has been formulated and applied to the keratinous fibres.

In a further aspect, then, the present disclosure concerns the use of an agent containing, in a cosmetic support,
(a) at least one direct dye,
(b) at least one amphoteric surfactant, in particular at least one alkylbetaine, and
(c) at least one alkylpolyglycoside, in particular at least one alkylpolyglucoside,
exemplified in that the content of amphoteric surfactant (b) in the agent—with respect to the total weight of the agent—is greater than the content of non-ionic surfactant (c), for the purposes of
increasing the chromaticity of dyes on keratinous fibres and/or increasing the colour uptake of dyes onto keratinous fibres and/or increasing the colour intensity of dyes on keratinous fibres, when colouring keratinous fibres, in particular human hair.

The statements pertaining to the agents apply mutatis mutandis to further preferred embodiments of the use.

The agents as contemplated herein may be used in a method for colouring human hair.

In a further aspect, then, the present disclosure concerns a method for increasing the chromaticity of dyes on keratinous fibres and/or increasing the colour uptake of dyes onto keratinous fibres and/or increasing the colour intensity of dyes on keratinous fibres.

when colouring human hair, in which an agent containing, in a cosmetic support,
(a) at least one direct dye,
(b) at least one amphoteric surfactant, in particular at least one alkylbetaine, and
(c) at least one alkylpolyglycoside, in particular at least one alkylpolyglucoside,
exemplified in that the content of amphoteric surfactant (b) in the agent—with respect to the total weight of the agent—is greater than the content of non-ionic surfactant (c),
is applied to the keratinous fibres.

The statements pertaining to the agents and uses apply mutatis mutandis to further preferred embodiments of the method.

In summary, the present disclosure is outlined in particular by the following points:

An agent for colouring keratinous fibres, in particular human hair, containing, in a cosmetic support,
(a) at least one direct dye,
(b) at least one amphoteric surfactant, in particular at least one alkylbetaine, and
(c) at least one alkylpolyglycoside, in particular at least one alkylpolyglucoside,
exemplified in that the total content with respect to weight of amphoteric surfactant (b) in the agent—with respect to the weight of the agent—is greater than the total content with respect to weight of alkylpolyglycoside (c).

The agent as hereinbefore described, wherein the total content—with respect to the weight of the agent—of amphoteric surfactants (b) and alkylpolyglycosides (c) is from about 1.0 to about 25.0% by weight, preferably from about 1.5 to about 20.0% by weight, of the agent.

The agent as hereinbefore described, wherein the agent comprises at least one amphoteric surfactant (b) in a total quantity of from about 0.5 to about 20.0% by weight, preferably from about 1.0 to about 14.5% by weight, with respect to the total weight of the agent.

The agent as hereinbefore described, wherein the agent comprises at least one alkylpolyglycoside (c) in a total quantity of from about 0.5 to about 14.5% by weight, preferably from about 1.5 to about 4.0% by weight, with respect to the total weight of the agent.

The agent as hereinbefore described, wherein the amphoteric surfactant (b) is an alkylbetaine, preferably an alkylamidoalkylbetaine, in particular a $C_{8-14}$ alkylamido-$(C_{2-6})$ alkylbetaine.

The agent as hereinbefore described, wherein the alkylpolyglycoside (c) is an alkylpolyglucoside, preferably an alkylpolyglucoside with an alkyl residue which comprises from about 10 to about 20 carbon atoms.

The agent as hereinbefore described, wherein the amphoteric surfactant (b) is an alkylamidoalkylbetaine, preferably cocamidopropylbetaine (($C_{11}H_{23}$)C(O)NH($C_3H_6$)N($NH_2$)$_2$ $CH_2C(O)O$), and the alkylpolyglycoside (c) is an alkylpolyglucoside, preferably laurylglycoside.

The agent as hereinbefore described, wherein the at least one direct dye is selected from a cationic direct dye, an anionic direct dye or a non-ionic direct dye.

The agent as hereinbefore described, wherein the at least one direct dye is selected from Basic Red 76, HC Blue 16, 4-hydroxypropylamino-3-nitrophenol, HC Red 13.

The agent as hereinbefore described, wherein the agent has a pH of from about 2 to about 11, preferably from about 3 to about 7.

The agent as hereinbefore described, wherein the agent furthermore comprises ≤0.2% by weight, with respect to the total weight of the agent, of surfactants which comprise a sulphate group (—$OSO_3$).

The agent as hereinbefore described, wherein the agent comprises ≤0.2% by weight, with respect to the total weight of the agent, of anionic surfactants.

The agent as hereinbefore described, wherein the agent furthermore comprises at least one associative thickening agent, preferably a non-ionic associative thickening agent, in particular cetylhydroxyethylcellulose, preferably in a quantity—with respect to the total weight of the agent—of from about 0.1 to about 5% by weight.

The agent as hereinbefore described, wherein the agent furthermore comprises at least one film-forming agent, in particular polyquaternium-37, preferably in a quantity—with respect to the total weight of the agent—of from about 0.1 to about 5% by weight.

The agent as hereinbefore described, wherein the agent comprises at least one non-ionic thickening agent, in particular cetylhydroxyethylcellulose, and at least one cationic polymer, in particular polyquaternium-37, in combination with each other.

An agent for colouring keratinous fibres, in particular human hair, containing, in a cosmetic support in the form of a shampoo,
(a) at least one direct dye,
(b) at least one amphoteric surfactant, in particular at least one alkylbetaine,
(c) at least one alkylpolyglycoside, in particular at least one alkylpolyglucoside,
(d) water, and
(e) at least one thickening agent,
preferably with the proviso that the agent is essentially free from sodium chloride,
exemplified in that the total content with respect to weight of amphoteric surfactant (b) in the agent—with respect to the weight of the agent—is greater than the total content with respect to weight of alkylpolyglycoside (c).

An agent for colouring keratinous fibres, in particular human hair, containing, in a cosmetic support in the form of a shampoo,
(a) at least one direct dye,
(b) at least one amphoteric surfactant, in particular at least one alkylbetaine,
(c) at least one alkylpolyglycoside, in particular at least one alkylpolyglucoside,
(d) water,
(e) at least one thickening agent, and
(f) at least one film-forming agent,
preferably with the proviso that the agent is essentially free from sodium chloride, exemplified in that the total content with respect to weight of amphoteric surfactant (b) in the agent—with respect to the weight of the agent—is greater than the total content with respect to weight of alkylpolyglycoside (c).

Use of an agent containing, in a cosmetic support,
(a) at least one direct dye,
(b) at least one amphoteric surfactant, in particular at least one alkylbetaine, and
(c) at least one alkylpolyglycoside, in particular at least one alkylpolyglucoside,
preferably with the proviso that the agent is essentially free from sodium chloride,
exemplified in that the total content with respect to weight of amphoteric surfactant (b) in the agent—with respect to the weight of the agent—is greater than the total content with respect to weight of alkylpolyglycoside (c), for the purposes of
increasing the chromaticity of dyes on keratinous fibres and/or
increasing the colour uptake of dyes onto keratinous fibres and/or
increasing the colour intensity of dyes on keratinous fibres,
when colouring keratinous fibres, in particular human hair.

A method for:
increasing the chromaticity of dyes on keratinous fibres and/or
increasing the colour uptake of dyes onto keratinous fibres and/or
increasing the colour intensity of dyes on keratinous fibres,
when colouring keratinous fibres, in particular human hair, in which an agent containing, in a cosmetic support,
(a) at least one direct dye,
(b) at least one amphoteric surfactant, in particular at least one alkylbetaine, and
(c) at least one alkylpolyglycoside, in particular at least one alkylpolyglucoside,
preferably with the proviso that the agent is essentially free from sodium chloride,
exemplified in that the total content with respect to weight of amphoteric surfactant (b) in the agent—with respect to the weight of the agent—is greater than the total content with respect to weight of alkylpolyglycoside (c),
is applied to the keratinous fibres.

The colouring agents as contemplated herein are exemplified by good foam formation properties which are comparable with conventional shampoos. Foam heights of more than about 2 cm can be obtained (fast foam test in a beaker).

The colouring agents as contemplated herein can be used to formulate toning shampoos which simultaneously include anionic, cationic and non-ionic direct dyes and utilize the entire colour range for every dye.

The use of the specific combination of amphoteric surfactants (b) and alkylpolyglycosides (c), wherein the total content with respect to weight of amphoteric surfactant (b) in the agent—with respect to the weight of the agent—is greater than the total content with respect to weight of alkylpolyglycoside (c), makes it possible to make significant improvements as regards colour uptake, chromaticity and/or colour intensity compared with the use of conventional anionic, cationic or amphoteric surfactants. Thus, surfactant-containing colorants can be provided which have a colour uptake which is comparable with that of aqueous colorants.

The agent may comprise a comparatively high proportion of amphoteric surfactant (b) and alkylpolyglycosides (c). These also act as emulsifying agents for the dyes, so that their solubility is enhanced, so that the organic solvent content in the colorant can be kept comparatively low.

EXAMPLES

The formulations summarized in Table 1 were produced. Unless indicated otherwise, the quantities are given as a percentage by weight with respect to the total weight. The figures relate to the active substance content.

TABLE 1

Composition of comparative test formulations V1, V2, V3 and V4, as well as of formulation E1 as contemplated herein

| Formulation | V1 | V2 | V3 | V4 | E1 |
|---|---|---|---|---|---|
| Sodium laureth-2-sulphate | | 5 | | | |
| Cocamido-propylbetaine (ex Dehyton K) | | | 5 | | |
| Cocamido-propylbetaine (ex Empigen ® Total Active TC/U) | | | | 5 | 5 |
| Laurylpoly-glycoside (Plantacare ®) | | | | | 3 |
| Direct dye (see Table 2) | 0.30 | 0.30 | 0.30 | 0.30 | 0.30 |
| NaCl | 0 | 0 | 0.25 | 0 | 0 |
| Water | 99.70 | 94.70 | 94.45 | 94.70 | 91.70 |
| pH | [4.3-5.0] | [4.3-5.0] | [4.3-5.0] | [4.3-5.0] | [4.3-5.0] |

The direct dyes summarized in Table 2 were used as direct dyes.

TABLE 2

Direct dyes employed

| Description of dye | Abbreviation used below |
|---|---|
| Basic Red 76 | A |
| HC Blue 16 | B |
| Basic Yellow 57 | C |
| 4-hydroxypropylamino-3-nitrophenol | D |
| HC Red 13 | E |

Colour uptake, colour intensity and chromaticity

Prior to the colouring process, hair strands (Kerling 10-0) were measured colorimetrically (Spectralflash SF 450 colorimetric instrument from Datacolor). Next, the ready-to-use colour formulations produced as described above were applied to the hair strands and left on for 30 minutes at 30° C. Next, the hair strands were thoroughly rinsed and dried in a stream of air. After colouring and drying, the hair strands were measured colorimetrically once again. Using the formula below, the difference in colour (ΔE) between uncoloured and coloured strands or the strands coloured with an aqueous solution of the dye and the strands coloured with the surfactant-containing colorant was calculated:

$$\Delta E = \sqrt{(Lv-Ln)^2 + (av-an)^2 + (bv-bn)^2}, \text{ in which}$$

Lv, av, bv are colorimetric values before colouring,
Ln, an, bn are colorimetric values after colouring.

In the same manner, the difference in colour (ΔE) between the strands coloured with an aqueous solution of the colour and the strands coloured with surfactant-containing colorants was calculated:

$$\Delta E = \sqrt{(Lw-Lt)^2+(aw-at)^2+(bw-bt)^2},\text{ in which}$$

Lw, aw, bw are after colouring with aqueous solution,
Lt, at, bt are after colouring with surfactant-containing colorant.

The chromaticity (chroma c, hue) was calculated from the parameters a (CIE) and b (CIE) using the following formula:

$$c=\sqrt{a^2+b^2}.$$

The measured and calculated data are summarized in Table 3.

The greater the difference in colour ΔE (vs. Kerling 10-0) between uncoloured strands and coloured strands, the stronger is the resulting colour uptake by the colour. Compared with each of the comparative formulations V1 to V4, an intense colour result was obtained for the dyes A, B, D and E when using formulations E1. A good colour result was obtained with dye C.

As high a chromaticity as possible (i.e. as high a value as possible for chroma c) indicates a high colour intensity. As can be seen from the calculated values, compared with each of the comparative formulations V1 to V4 for the colours A, B, D and E, the highest value for chroma C was determined when using the formulation E1. A good chromaticity was also obtained for dye C.

The measured value ΔE (compared with aqueous colorant) describes the trueness of colour of colouring by employing a surfactant-containing solution compared with colouring alone by employing an aqueous solution. Low values point to a colour uptake from surfactant-containing solution which is similar to that from aqueous solution. Compared with the colour uptake from aqueous solution, the formulation E1 also produced good values for all of the test dyes. In the case of dye C, these were even better than all of the other formulations.

The measured value L (CIE) is a measure of the lightness or intensity of a colour. Small measured values represent a high intensity. The smaller the value of L, the greater is the colour intensity. Compared with formulations V1 and V4, for formulation E1, good to very good values for L (CIE) were measured throughout. An extraordinarily low value for L was obtained with dye E.

TABLE 3

Results of colorimetric tests on formulations V1, V2, V3, V4 and E1 with the dyes A, B, C, D and E

| Dye | Formulation | L (CIE) | a (CIE) | b (CIE) | Chroma c | ΔE (vs. Kerling 10-0) | ΔE (vs. aqueous colorant) |
|---|---|---|---|---|---|---|---|
| A | V1 | | | | 55.90 | 62.13 | |
| A | V2 | 68.74 | 17.96 | 18.80 | 26.00 | 19.26 | 44.40 |
| A | V3 | 40.71 | 50.85 | 35.96 | 62.28 | 64.39 | 7.49 |
| A | V4 | 38.66 | 50.36 | 35.64 | 61.70 | 65.13 | 6.12 |
| A | E1 | 39.80 | 51.25 | 36.37 | 62.84 | 65.33 | 7.59 |
| B | V1 | | | | 33.02 | 75.68 | |
| B | V2 | 68.35 | −4.63 | 7.97 | 9.21 | 15.41 | 62.70 |
| B | V3 | 26.59 | 6.83 | −34.91 | 35.58 | 74.47 | 7.05 |
| B | V4 | 21.46 | 10.85 | −33.23 | 34.96 | 77.33 | 2.02 |
| B | E1 | 23.25 | 11.05 | −35.63 | 37.30 | 77.73 | 4.59 |
| C | V1 | | | | 71.16 | 53.31 | |
| C | V2 | 75.59 | 1.71 | 22.96 | 23.03 | 4.49 | 49.00 |
| C | V3 | 70.82 | 6.25 | 62.01 | 62.33 | 43.85 | 11.23 |
| C | V4 | 66.62 | 14.52 | 71.81 | 73.26 | 55.61 | 2.44 |
| C | E1 | 68.90 | 12.26 | 70.74 | 71.80 | 53.66 | 2.06 |
| D | V1 | | | | 52.65 | 58.1 | |
| D | V2 | 43.53 | 44.86 | 28.26 | 53.02 | 56.40 | 3.19 |
| D | V3 | 44.64 | 44.25 | 27.84 | 52.28 | 55.18 | 4.30 |
| D | V4 | 46.01 | 44.54 | 26.91 | 52.04 | 54.47 | 5.78 |
| D | E1 | 43.61 | 46.79 | 27.99 | 54.52 | 57.83 | 3.96 |
| E | V1 | | | | 17.91 | 52.14 | |
| E | V2 | 47.40 | 15.72 | 3.28 | 16.06 | 37.15 | 15.79 |
| E | V3 | 38.91 | 17.51 | 0.98 | 17.54 | 45.81 | 6.89 |
| E | V4 | 32.03 | 17.91 | −4.27 | 18.41 | 53.93 | 4.35 |
| E | E1 | 28.91 | 18.94 | −5.98 | 19.86 | 57.63 | 6.92 |

Overall, the formulation E1 as contemplated herein exhibits outstandingly good properties compared with conventional formulations as regards colour uptake, colour intensity and chromaticity.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. An agent for colouring keratinous fibres comprising, in a cosmetic support,
   (a) at least one direct dye,
   (b) cocoamidopropyl betaine, and
   (c) lauryl glucoside,
   wherein the total content of (b) in the agent—with respect to the weight of the agent—is greater than the total content of (c).

2. The agent as claimed in claim 1, wherein the total content of (b) and (c) together amounts to from about 1.5% to about 20.0% by weight.

3. The agent as claimed in claim 1, comprising (b) in a total quantity of from about 2.0% to about 9.5% by weight and (c) in a total quantity of from about 1.0 to about 6.7% by weight.

4. The agent as claimed in claim 1, wherein the direct dye comprises basic red 76.

5. The agent as claimed in claim 1, wherein the direct dye comprises HC blue 16.

6. The agent as claimed in claim 1, wherein direct dye comprises basic yellow 57.

7. The agent as claimed in claim 1, wherein the direct dye comprises 4-hydroxypropyylamino-3-nitrophenol.

8. The agent as claimed in claim 1, wherein the direct dye comprises HC red 13.

9. The agent as claimed in claim 1, wherein the agent comprises ≤0.2% by weight, with respect to the total weight of the agent, of anionic surfactants.

10. The agent as claimed in claim 1, comprising the direct dye (a) in a total quantity of from about 0.001 to about 7% by weight, with respect to the weight of the agent.

11. The agent as claimed in claim 1, wherein the agent further comprises at least one associative thickening agent, in a quantity—with respect to the total weight of the agent—of from about 0.1 to about 5% by weight.

12. The agent as claimed in claim 1, wherein the agent further comprises at least one film-forming agent, in a quantity—with respect to the total weight of the agent—of from about 0.1 to about 5% by weight.

13. The agent as claimed in claim 1, wherein the agent comprises at least one non-ionic associative thickening agent and at least one cationic polymer, in combination with each other.

14. A method for colouring keratinous fibres, comprising applying an agent as claimed in claim 1 to the keratinous fibres.

15. An agent for colouring keratinous fibres comprising, in a cosmetic support,
   (a) at least one direct dye in a total quantity of from about 0.6 to about 1% by weight, with respect to the weight of the agent;
   (b) an alkylbetaine selected from $((C_{10}H_{21})C(O)NH(C_3H_6)N(NH_2)_2CH_2C(O)O)$, $((C_{11}H_{23})C(O)NH(C_3H_6)N(NH_2)_2CH_2C(O)O)$, and $((C_{12}H_{25})C(O)NH(C_3H_6)N(NH_2)_2CH_2C(O)O)$ in a total quantity of from about 3.0 to 7.0% by weight, with respect to the weight of the agent; and
   (c) an alkyl glucoside selected from lauryl glucoside and decyl glucoside in a total quantity of from about 1.5 to about 4.0% by weight, with respect to the weight of the agent;
   wherein the total content of (b) in the agent—with respect to the weight of the agent—is greater than the total content of (c).

16. The agent as claimed in claim 15, wherein the amphoteric surfactant (b) is cocamidopropylbetaine $((C_{11}H_{23})C(O)NH(C_3H_6)N(NH_2)_2CH_2C(O)O)$ and the alkylglucoside (c) is laurylglucoside.

17. The agent according to claim 16, wherein the direct dye comprises basic red 76.

18. The agent according to claim 16, wherein the direct dye comprises HC blue 16.

19. The agent according to claim 16, wherein the direct dye comprises basic yellow 57.

20. The agent according to claim 16, wherein the direct dye comprises 4-hydroxypropylamine-3-nitrophenol.

21. The agent according to claim 16, wherein the direct dye comprises HC red 13.

* * * * *